United States Patent
Obata et al.

(10) Patent No.: US 7,349,727 B2
(45) Date of Patent: Mar. 25, 2008

(54) LIVING BODY LIGHT MEASURING DEVICE

(75) Inventors: Akiko Obata, Hatoyama (JP); Atsushi Maki, Fuchu (JP); Kanehisa Morimoto, Ashiya (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/348,441

(22) Filed: Feb. 7, 2006

(65) Prior Publication Data

US 2006/0241361 A1 Oct. 26, 2006

(30) Foreign Application Priority Data

Apr. 22, 2005 (JP) ............................. 2005-125030

(51) Int. Cl.
*A61B 5/00* (2006.01)
(52) U.S. Cl. ...................... 600/340; 600/310; 600/322
(58) Field of Classification Search ................ 600/310, 600/322, 323, 340, 309
See application file for complete search history.

(56) References Cited

U.S. PATENT DOCUMENTS

| | | | | |
|---|---|---|---|---|
| 5,515,847 | A * | 5/1996 | Braig et al. ................. | 600/316 |
| 5,803,909 | A * | 9/1998 | Maki et al. ................. | 600/310 |
| 6,174,283 | B1 * | 1/2001 | Nevo et al. ................. | 600/301 |
| 6,519,486 | B1 * | 2/2003 | Edgar et al. ................ | 600/336 |
| 6,615,065 | B1 * | 9/2003 | Barrett et al. .............. | 600/340 |
| 7,142,902 | B2 * | 11/2006 | Eda et al. ................... | 600/340 |
| 2004/0059236 | A1 | 3/2004 | Margulies et al. | |
| 2004/0171919 | A1 * | 9/2004 | Maki et al. ................. | 600/310 |
| 2004/0210119 | A1 * | 10/2004 | Eda et al. .................. | 600/340 |

(Continued)

FOREIGN PATENT DOCUMENTS

EP 1 452 136 A1 1/2004

(Continued)

OTHER PUBLICATIONS

Obata, A. et al, "Acute effects of alcohol on hemodynamic changes during visual stimulation assessed using 24-channel near-infrared spectroscopy", Elsevier, Psychiatry Research Neuroimaging, Science Direct, 2003, pp. 145-152.

(Continued)

*Primary Examiner*—Eric Winakur
*Assistant Examiner*—Etsub D Berhanu
(74) *Attorney, Agent, or Firm*—Reed Smith LLP; Stanley P. Fischer, Esq.; Juan Carlos A. Marquez, Esq.

(57) ABSTRACT

There is provided a living body light measuring device capable of monitoring a time curve of a blood substance concentration as time curves of parameters of a signal waveform and judging or analyzing characteristic traits of a subject relevant to the parameters of the signal waveform, wherein a signal processor extracts parameters such as a peak value and latency from a hemoglobin signal waveform measured before and after substance intake of a testee, and generates and displays a time curve graph having a parameter and time respectively as its ordinate and abscissa. Influence of an intake substance upon blood component concentrations and blood flow can be monitored by monitoring the time curves of parameters of the signal waveform. A category processor classifies measurement data into categories, analyzes time curves of a plurality of parameters every category, and displays a result on a result viewer.

8 Claims, 10 Drawing Sheets

U.S. PATENT DOCUMENTS

2005/0177033 A1    8/2005  Kawasaki

FOREIGN PATENT DOCUMENTS

JP          2002-177281      12/2000
WO     WO 2004/034895 A1    10/2003

OTHER PUBLICATIONS

Obata, A. et al, "Effects of alcohol on hemodynamic and cardio-vascular reaction in different genotypes", Elsevier, Psychiatry Research Neuroimaging, Science Direct, 2005, pp. 65-72.

* cited by examiner

【PEAK VALUE】

PEAK VALUE CHANGE AFTER ORAL INTAKE OF TRAPIDIL

PEAK VALUE CHANGE BEFORE AND AFTER DOXAZOCIN INTAKE

PROCESSING FLOW CHART (A) PROVIDING DATA WITH CATEGORY INFORMATION (B) SELECT DISPLAY OF CATEGORIZED ANALYSIS RESULT

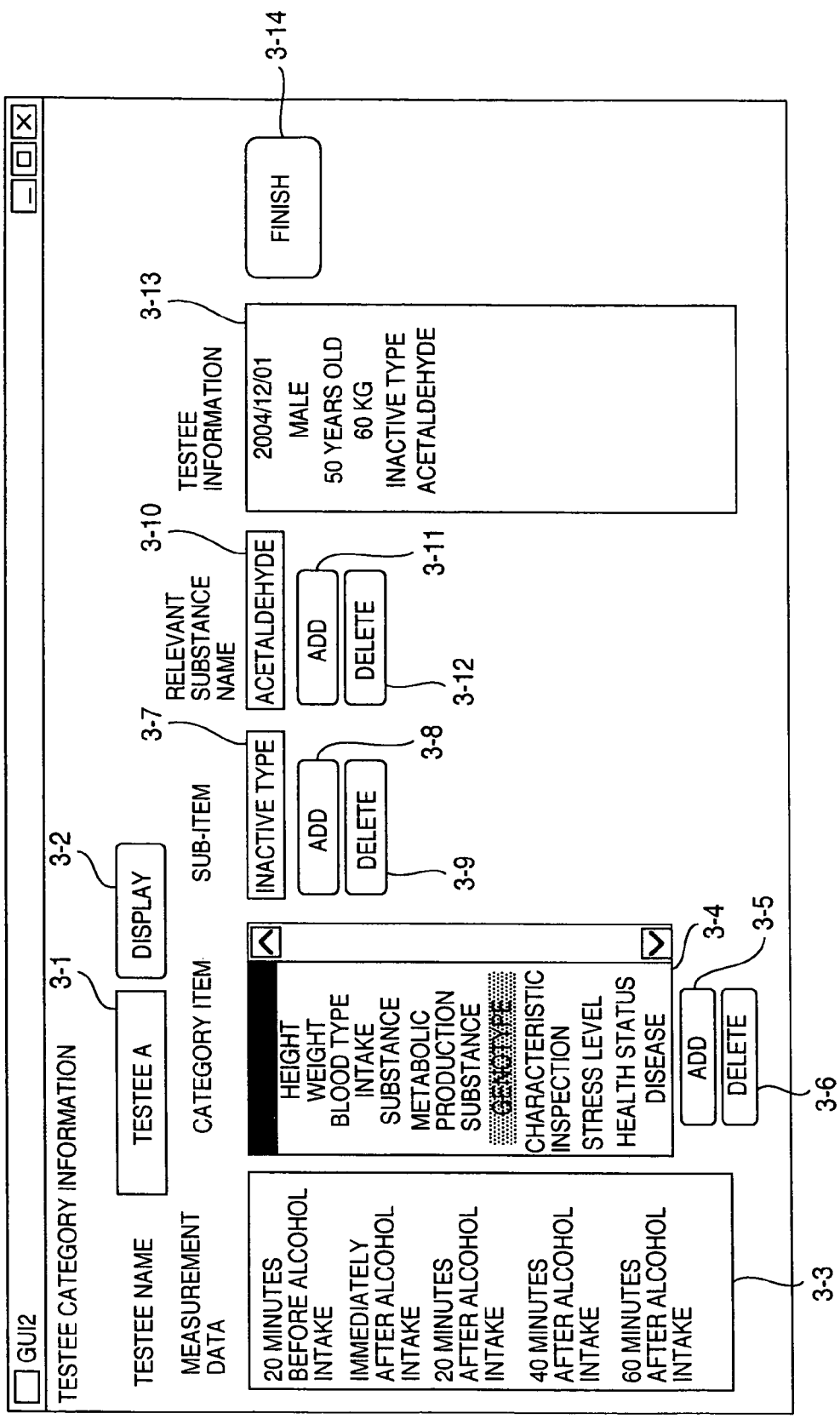

LIVING BODY LIGHT MEASURING DEVICE

INCORPORATION BY REFERENCE

The present application claims priority from Japanese application JP2005-125030 filed on Apr. 22, 2005, the content of which is hereby incorporated by reference into this application.

BACKGROUND OF THE INVENTION

The present invention relates to a device (living body light measuring device) for irradiating a human head with light, measuring light reflected or scattered within the head near the surface (hereafter referred to also as living body transmitted light), and thereby measuring a higher brain function.

The living body light measuring device is a device for detecting living body transmitted light using light in the range of visible to near infrared rays, and measuring the living body function in a non-invasive manner. In recent years, living body light measuring devices for irradiating light from a plurality of positions by using optical fibers, measuring a living body transmitted light intensity at a plurality of detection points, obtaining information of a comparatively wide area including these detection points, and imaging the brain function have been developed. It is attempted to apply these living body light measuring devices to the study of the brain function and clinical use.

Information obtained in such a living body light measuring device is a signal corresponding to a change of a substance (such as hemoglobin) in blood between before and after a trial, when a stimulation or a task (trial) such as a language stimulation, a flash stimulation, or finger tapping is given mainly to a living body a plurality of times. Such a change signal of hemoglobin which is a substance in blood is displayed every measurement channel typically as a graph (signal waveform) indicating a time course or as an image called topography obtained by coupling values at measurement points in a contour line form.

As a result of accumulation of studies on relevancies between the signal waveform and the brain function, a living body light measuring device having a function of making a decision on brain diseases or mental diseases on the basis of a feature extracted from the signal waveform is also developed (US2005/0177033 corresponding to JP-A-2003-275191). Furthermore, a technique of conducting a quantitative analysis on the signal waveform and generating quantitative data is also proposed (JP-A-2002-177281). In US2005/0177033, a technique of representing a feature such as a peak value or a latency as a template on the basis of the measurement waveform of the hemoglobin signal, comparing a feature pattern of a healthy person with a feature pattern of a mental disease patient, and assisting in diagnosing a mental disease is disclosed.

Until now, brain function measurements using living body light measurement are based mainly on the relevancies between the change waveform of a substance in blood before and after the load such as stimulation and the brain function. In recent years, it has been found that the hemoglobin signal waveform is also changed by metabolism of substances in the living body. It is desired to develop a living body light measuring device capable of analyzing its physiological meaning and conducting display associated with parameters of the hemoglobin signal waveform. When alcohol intake is conducted, the hemoglobin waveform is changed according to a time curve of blood acetaldehyde concentration, which is an alcohol metabolic substance, or endocrine hormones, by the aldehyde dehydrogenase 2 genotype concerning aldehyde dehydrogenase. This phenomenon is reported.

In the conventional living body light measuring device, the hemoglobin signal waveform which is measurement data is displayed only as a time course, an average value, or a topography. A hemoglobin signal waveform relating to a time curve of a metabolic substance cannot be monitored.

Parameters (features) representing the hemoglobin signal waveform are considered to have relevancies to various physiological reactions. In the conventional living body light measuring device, however, it is not possible to analyze these relevancies and judge characteristic traits of a specific testee on the basis of a result of the analysis.

SUMMARY OF THE INVENTION

Therefore, an object of the present invention is to provide a living body light measuring device capable of monitoring a time curve of a blood substance concentration.

Another object of the present invention is to provide a living body light measuring device capable of judging characteristic traits of a subject relating to time curves of parameters in a signal waveform or analyzing the characteristic traits.

In order to achieve the object, a living body light measuring device according to a first aspect of the present invention includes light measuring means for applying light to a subject and receiving light reflected or transmitted by a head of the subject, signal processing means for drawing a change of a blood substance when a trial is given to the subject a plurality of times, as a signal waveform on the basis of a measurement signal received by the light measuring means, and result viewer means for displaying a result of processing conducted by the signal processing means. The signal processing means extracts at least one feature from each of a plurality of signal waveforms measured at predetermined time intervals, and causes the result viewer means to display a time curve of the feature.

The feature extracted by the signal processing means includes, for example, a peak value of the signal waveform, and a time period (latency) between start time of the trial and time when the signal waveform arrives at the peak value.

The time curve of the feature that the signal processing means causes the result viewer means to display is, for example, a graph having time as an abscissa axis thereof and a value (feature quantity) obtained by converting the feature to a numerical value as an ordinate axis thereof.

A living body light measuring device according to a second aspect of the present invention includes light measuring means for applying light to a subject and receiving light reflected or transmitted by a head of the subject, signal processing means for drawing a change of a blood substance when a trial is given to the subject a plurality of times, as a signal waveform on the basis of a measurement signal received by the light measuring means, result viewer means for displaying a result of processing conducted by the signal processing means, and input means for sending a command to the signal processing means. The input means includes means for inputting specification of a specific inspection item among a plurality of inspection items. The signal processing means extracts at least one feature corresponding to a specific inspection item specified by the input means, and causes the result viewer means to display a time curve of the feature as a graph.

In the living body light measuring device according to the present invention, the signal processing means includes storage means for storing data, the data accumulating relations between sub-items belonging to the inspection item and the time curve, and screening means for judging characteristic traits of the subject on the basis of the graph and the accumulated data obtained as to the subject.

Furthermore, the inspection items are classified according to an intake substance of the subject, and data measured at predetermined time intervals include data before and after substance intake time of the subject.

A living body light measuring device according to a third aspect of the present invention includes light measuring means for applying light to a subject and receiving light reflected or transmitted by a head of the subject, signal processing means for drawing a change of a blood substance when a trial is given to the subject a plurality of times, as a signal waveform on the basis of a measurement signal received by the light measuring means, result viewer means for displaying a result of processing conducted by the signal processing means, and input means for sending a command to the signal processing means. The input means includes means for inputting specification of a plurality of inspection conditions comprising subject information and inspection items. The signal processing means includes means for classifying a signal waveform measured at predetermined time intervals, on the basis of an inspection condition specified by the input means, and means for selecting measurement data corresponding to the inspection condition specified by the input means and causing the result viewer means to display a time curve of at least one feature of the measurement data as a graph.

According to the present invention, it is possible to monitor a time curve of a substance in blood, such as hemoglobin, by displaying a graph having a parameter (feature) featuring a signal waveform of the substance in blood as its ordinate axis and time as its abscissa axis. As a result, it is possible to monitor a time curve of the higher brain function activity relevant to a time curve of the substance in blood and a time curve of dynamics of a metabolic substance or the like in a living body. Furthermore, it is possible to analyze relevancies between various characteristic traits and the time curves of the parameters by storing data of the time curves of the parameters concerning various subject characteristic traits (such as physical and psychological features, diseases and genotypes) to be inspected. It is also possible to judge the characteristic traits as to the testee who becomes an object of the inspection on the basis of the analyzed data.

In addition, according to the present invention, data measured under diversified measurement conditions are classified into categories and then analyzed, and a result is displayed. Accordingly, the trouble and time caused by the analysis processing of the operator can be reduced remarkably.

Other objects, features and advantages of the invention will become apparent from the following description of the embodiments of the invention taken in conjunction with the accompanying drawings.

BRIEF DESCRIPTION OF THE DRAWINGS

FIG. 9 is a diagram showing a category information input screen in the embodiment shown in FIGS. 8A to 8C;

DESCRIPTION OF THE EMBODIMENTS

Hereafter, embodiments of a living body light measuring device according to the present invention will be described with reference to the drawings.

Figure 1:
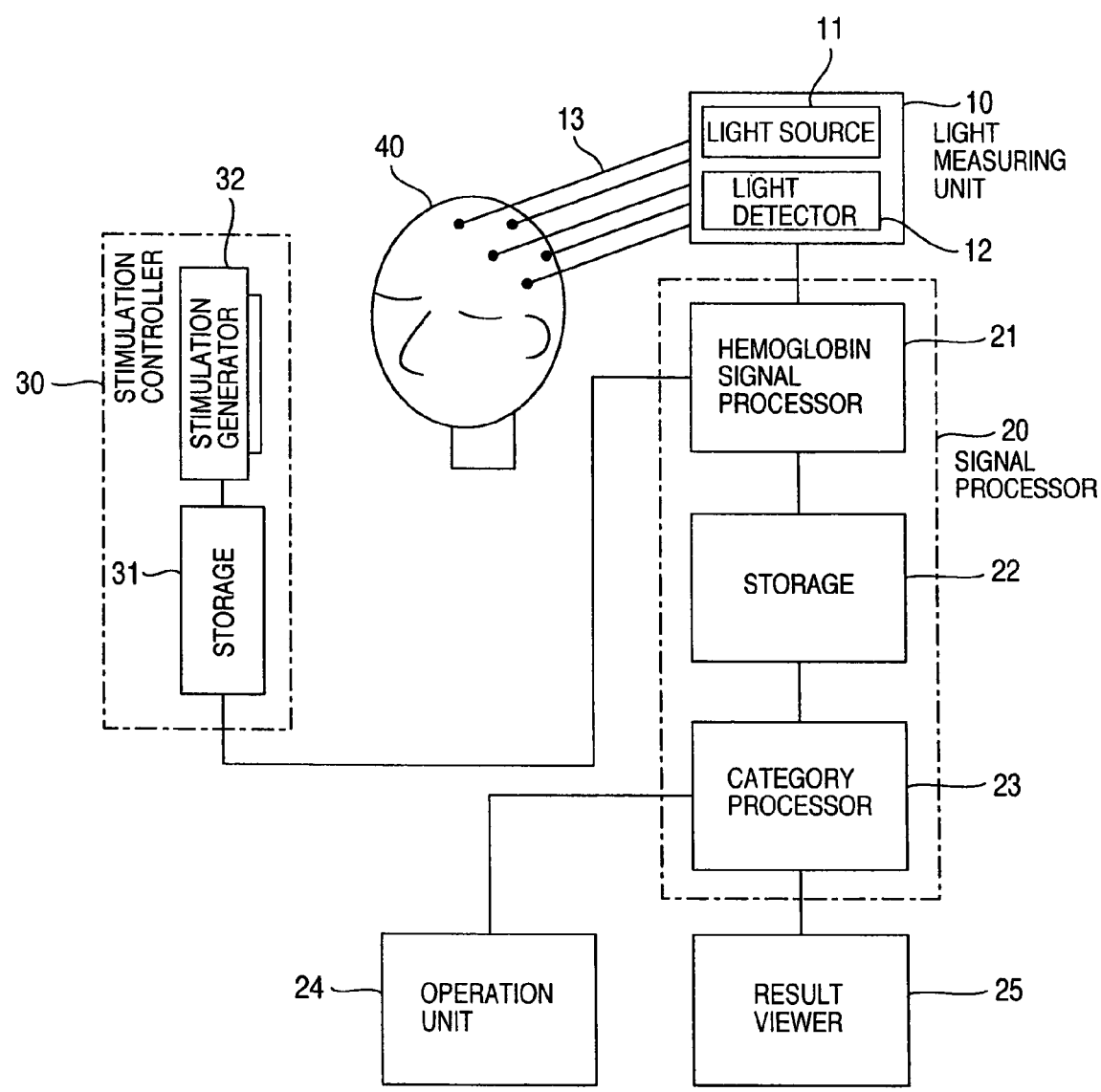
FIG. 1 is a diagram showing a general configuration of a living body light measuring device according to the present invention.

FIG. 1 is a general block diagram showing a living body light measuring device according to the present invention. The living body light measuring device mainly includes a light measuring unit 10, a signal processor 20, and a stimulation controller 30.

The light measuring unit 10 includes a light source unit 11 and a light detector 12. The light source unit 11 includes a light source such as a laser for generating light having a predetermined wavelength, a light modulator for modulating light generated by the light source to as light beams having as many different frequencies as the number of measurement points, and optical fibers 13 for leading the modulated light beams to a surface of a head of a subject 40. Wavelengths of light generated by the light source 11 are 780 nm and 830 nm when the blood substance to be measured is hemoglobin (oxy-Hemoglobin and deoxy-Hemoglobin). If the substance to be measured is different, different wavelengths can be adopted. In the present embodiment, the case where the blood substance is hemoglobin will be described.

The measurement points in the living body light measurement are points located nearly in the middle between light irradiation positions and light detection positions. Positions and the number of the measurement points depend upon the number and arrangements of the light irradiation positions and the light detection positions. Typically, a plurality of light irradiation positions and a plurality of light detection positions are arranged alternately on points of a matrix having a configuration of 3 by 3, 4 by 4 or the like. In the case of the 3 by 3 matrix, the number of measurement points becomes 12. In application of the present invention, it is not always necessary to have a plurality of measurement points. Using data from a plurality of measurement points, however, a more accurate analysis can be conducted.

The light detector 12 includes light receiving elements for receiving light beams from the optical fibers 13 having tips arranged in the light detection positions, and a detection circuit for discriminating the received light beam on the basis of modulation frequencies, and generating hemoglobin change signals every measurement point.

The signal processor 20 includes a hemoglobin signal processor 21 for conducting time series processing (generation of time course data) of the change of the blood circulation dynamics in the living body and imaging tomography (generation of a signal waveform) on a hemoglobin change signal, a storage 22 for storing measurement data obtained after the signal processing, and a category processor 23 for conducting classification processing on measurement data according to inspection conditions such as subject information and inspection items. As external devices, the signal processor 20 further includes an operation unit 24, such as a keyboard and a mouse, for inputting a command required for processing conducted in the hemoglobin signal processor 21 and the category processor 23, and a result viewer 25 for displaying an image obtained as a result of processing conducted in the hemoglobin signal processor 21 or the category processor 23. The result viewer 25 conducts display of a GUI linked with the operation unit 24 besides display of a result image.

Besides the above-described time series processing and imaging, on the basis of a command given by the operation unit 24, the signal processor 20 conducts processing for calculating parameters (features) from the formed change waveform, processing for imaging time curves of the parameters as regards data obtained from the same subject at predetermined time intervals, and judgment processing for analyzing the time curves of the parameters and judging characteristic traits of the subject in an inspection category.

The stimulation controller 30 is a device for controlling stimulation given to the subject 40. The stimulation controller 30 includes a storage 31 for storing an image, a sound, a voice, speech data or the like for stimulation as analog or digital data, a stimulation generator 32 such as a speaker or a PC screen for exhibiting the image, sound, voice, speech data or the like for stimulation to the subject, and a controller (not illustrated) for controlling generation timing of stimulation from the stimulation generator. Such stimulation controller 30 may be provided as a part of the living body measuring device. However, the stimulation controller 30 may be provided as an independent device. In that case, information such as timing, time, or hour at which stimulation is issued is sent to the living body light measuring device (the signal processor 20 therein). Or an order may be sent from the living body light measuring device to the stimulation controller 30. In response to this order, ordered stimulation among the image, sound, voice, and speech data stored in the storage is generated with ordered timing and time.

Operation of the living body light measuring device in such a configuration will now be described.

In the ensuing description, the embodiment will be described by taking measurement under the alcohol intake condition as an example.

It is known that the alcohol intake causes the blood concentration of acetaldehyde which is an alcohol metabolic substance to rise, the vascular reaction to be affected, and endocrine hormones of several kinds to be discharged. These living body reactions differ from person to person. This is because the action of an enzyme that breaks down acetaldehyde differs hereditarily genetically. It is called ALDH2 genotype (active type ALDH2*1/1 and inactive type ALDH2*1/2). In the present embodiment, therefore, the case where ALDH2 genotype is selected as an inspection item and measurement is conducted will be described.

Figure 2:
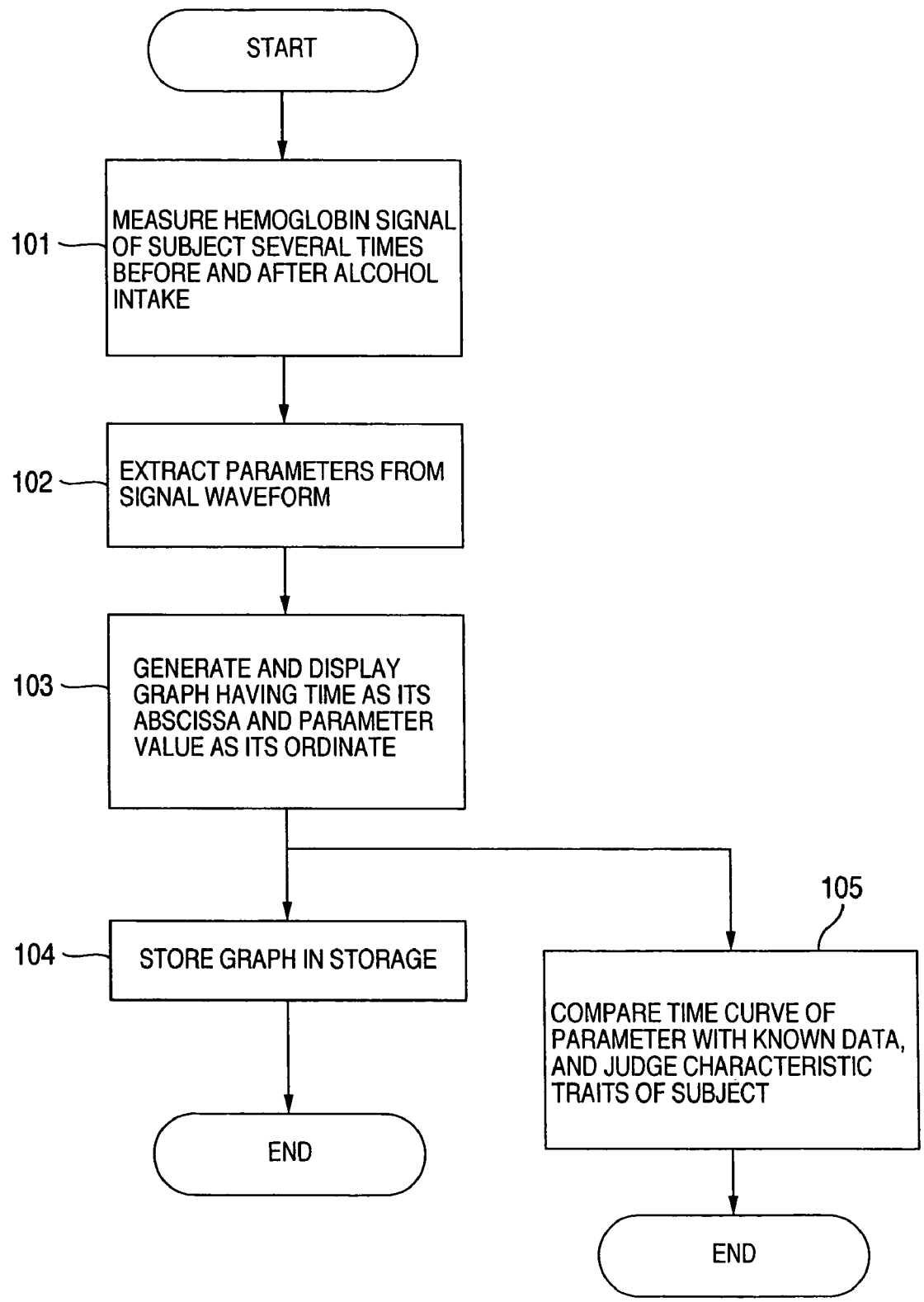
FIG. 2 is a flow diagram showing an embodiment of a measurement procedure using a living body light measuring device according to the present invention.

FIG. 2 is a flow diagram showing an operation procedure. In the beginning, a hemoglobin signal of a subject is measured (step 101). The hemoglobin signal measurement is conducted before alcohol intake into the subject, immediately after the alcohol intake, and a predetermined time after the alcohol intake (for example, 20 minutes, 40 minutes, or 60 minutes after the alcohol intake). As for the measurement, a trial includes a pair of a stimulation period and a rest period for the stimulation controller 30. A hemoglobin change signal over the periods is obtained as a signal waveform. Typically, the trial is conducted a plurality of times, and signal waveforms conducted respective times are averaged. In order to make parameter extraction accurate, filter processing and baseline process are conducted as occasion demands.

Figure 3:
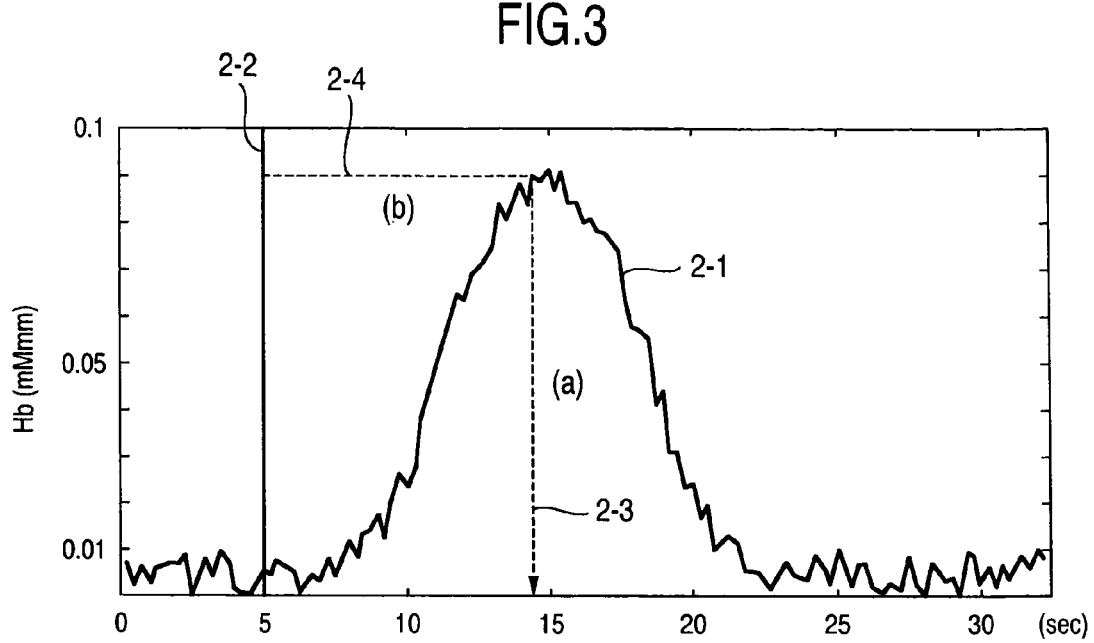
FIG. 3 is a diagram showing a signal waveform generated from a hemoglobin signal and its parameters.

An example of a hemoglobin signal waveform obtained in the light measuring unit 10 is shown in FIG. 3. In FIG. 3, the abscissa axis indicates time and corresponds to length of one pair of trial. The ordinate axis represents a value obtained by converting a signal change applied to a signal obtained before conducting a trial to a hemoglobin quantity change, and has mMmm as the unit. A time axis 2-2 represents time when stimulation is started. As illustrated, a hemoglobin signal waveform 2-1 rises when stimulation is started, and returns to its original signal value via a peak value 2-3. Such a hemoglobin signal waveform can be featured by, for example, a time period 2-4 between time of stimulation start and time when the waveform arrives at the peak value (referred to as latency), the peak value 2-3, an integral value (area) of the waveform between the stimulation start time and the peak value, its differential value, an integral value (area) of the waveform between the peak value and the original signal value, its differential value, an average of a change quantity, or the like. According to the inspection item, one or more parameters which become an index optimum to the decision are selected. In the present embodiment in which the inspection item is ALDH2 genotype, the peak value and the latency are selected as parameters (step 102).

In FIG. 3, only a result obtained from a hemoglobin signal at one measurement point (measurement channel) is shown. However, similar processing can be conducted on other measurement points as well. The above-described parameters may be found from a waveform obtained by applying arithmetical mean calculation to all measurement points. Alternatively, two or more specific measurement points may be selected. The parameters may be found from a waveform obtained by applying arithmetical mean calculation to time series data which are in turn obtained by giving stimulation a plurality of times. Alternatively, the parameters may be found from a waveform of a hemoglobin signal obtained by a specifically selected stimulation.

As for processing for finding parameters from a signal waveform, i.e., extraction of parameters, for example, a feature extraction technique described in JP-A-2003-275191 can be used. The signal processor 20 conducts such parameter extraction on hemoglobin change waveforms obtained by measurements conducted in time series, and generates a graph having measurement time as its abscissa and a parameter as its ordinate. The generated graph is displayed on the result viewer 25 (step 103). The measurement data and the generated graph are stored in the storage 22 as occasion demands, for later analysis (step 104).

Figure 4:
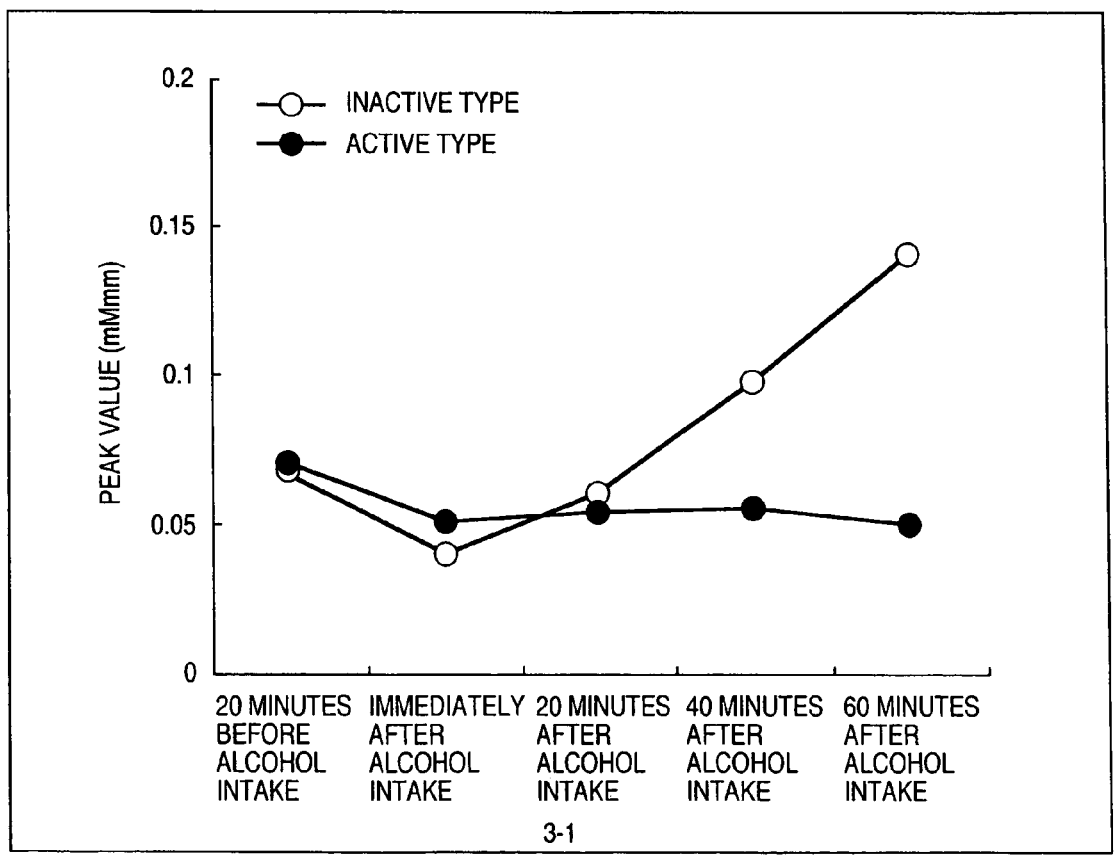
FIG. 4 is a diagram showing time curves of a peak value of a signal waveform in alcohol intake and measurement.
Figure 5:
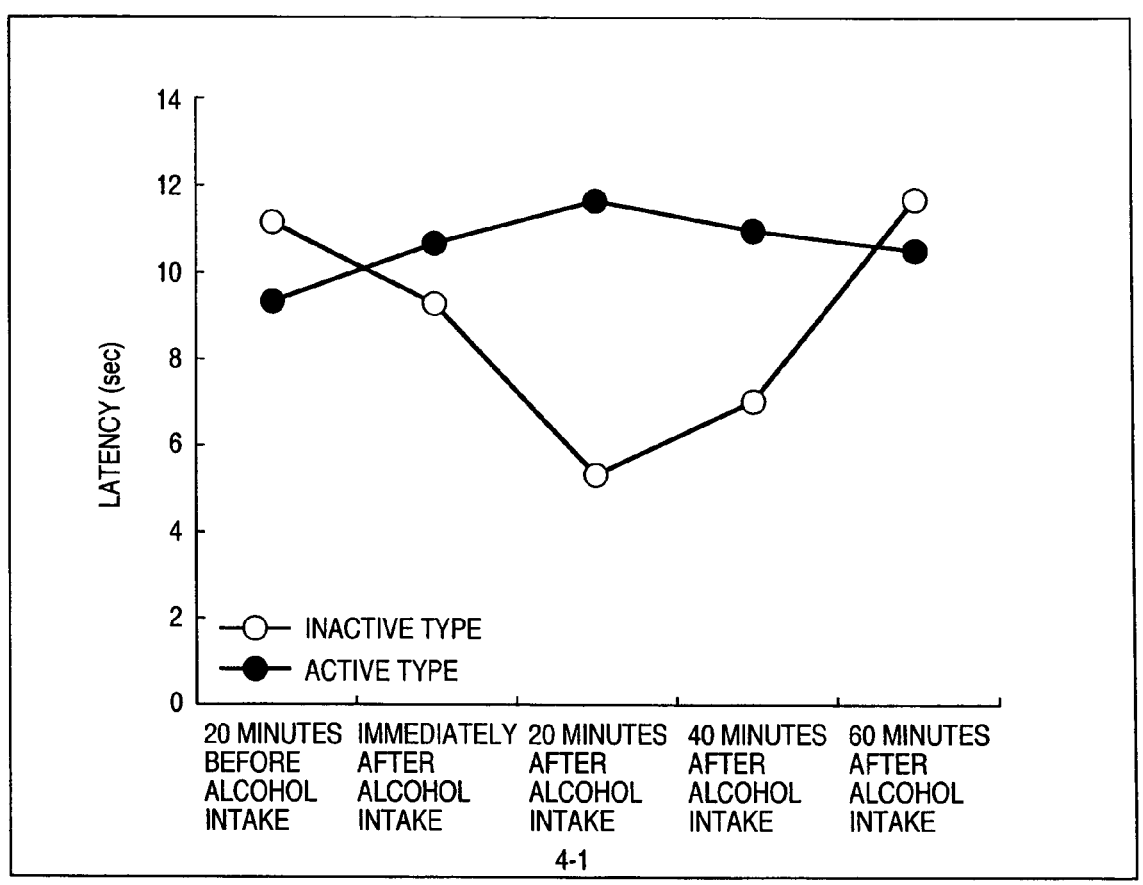
FIG. 5 is a diagram showing time curves of a latency of a signal waveform in alcohol intake and measurement.

Graphs respectively representing time curves of the peak value and latency with respect to the active type and inactive type of the ALDH2 genotype are shown in FIGS. 4 and 5, respectively. As shown in FIGS. 4 and 5, in the active type, there is little variation with time elapse in both the peak value and latency. On the other hand, in the inactive type, great variation is observed. If a person has knowledge of the time curves concerning a predetermined inspection item such as the ALDH2 genotype, therefore, the person can determine whether the testee is the active type or the inactive type, because time curve graphs of the parameters shown in FIGS. 4 and 5 are displayed (step 105).

According to the present embodiment, time curves of parameters of signal waveforms are thus displayed according to the inspection item. Therefore, a substance relevant to the inspection item can be indirectly monitored. For example, in the case of the ALDH2 genotype, blood aldehyde concentration can be indirectly monitored. Furthermore, it becomes possible to judge characteristic traits of the subject in the inspection item, such as whether the ALDH2 genotype is the active type or inactive type.

Figure 6:
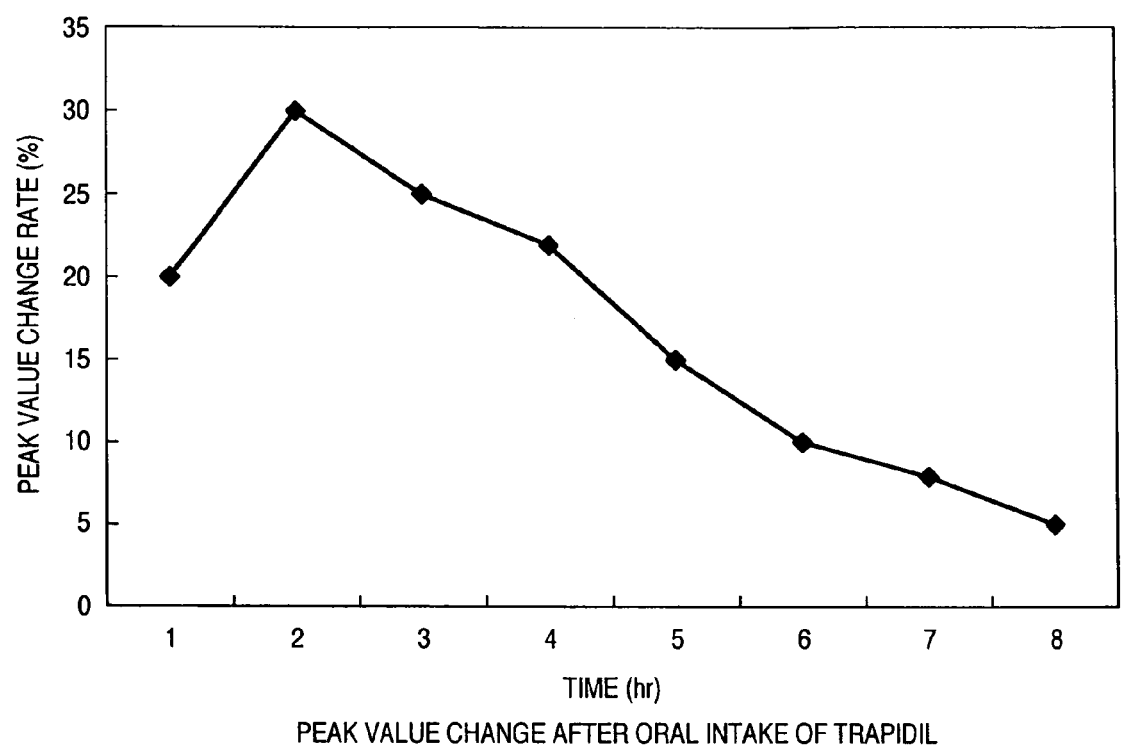
FIG. 6 is a diagram showing a time curve of a peak value of a signal waveform after oral intake of trapidil.

The embodiment has been described by taking the ALDH2 genotype as an example of the inspection item. However, characteristic traits or an intake medicine having relevancy to the blood concentration or a blood flow change can be made an object of inspection. For example, trapidil is a vasodepressor which acts on the blood smooth muscle and increases the blood flow. A change corresponding to a movement of such a vasodepressor in a living body cannot be ascertained unless, for example, blood is drawn and concentration in blood plasma is monitored. Using the living body light measuring device according to the present invention, as shown in FIG. 6, it is possible to monitor the change from time curves of the peak value and latency of the hemoglobin signal waveform measured a plurality of times in a non-invasive manner.

It is known that the α1 blocker blocks an α1 receptor in the artery system under adjustment of the sympathetic system and suppresses the artery shrinking action, but the cardiac performance is not suppressed and blood flows of organs increase.

Figure 7:
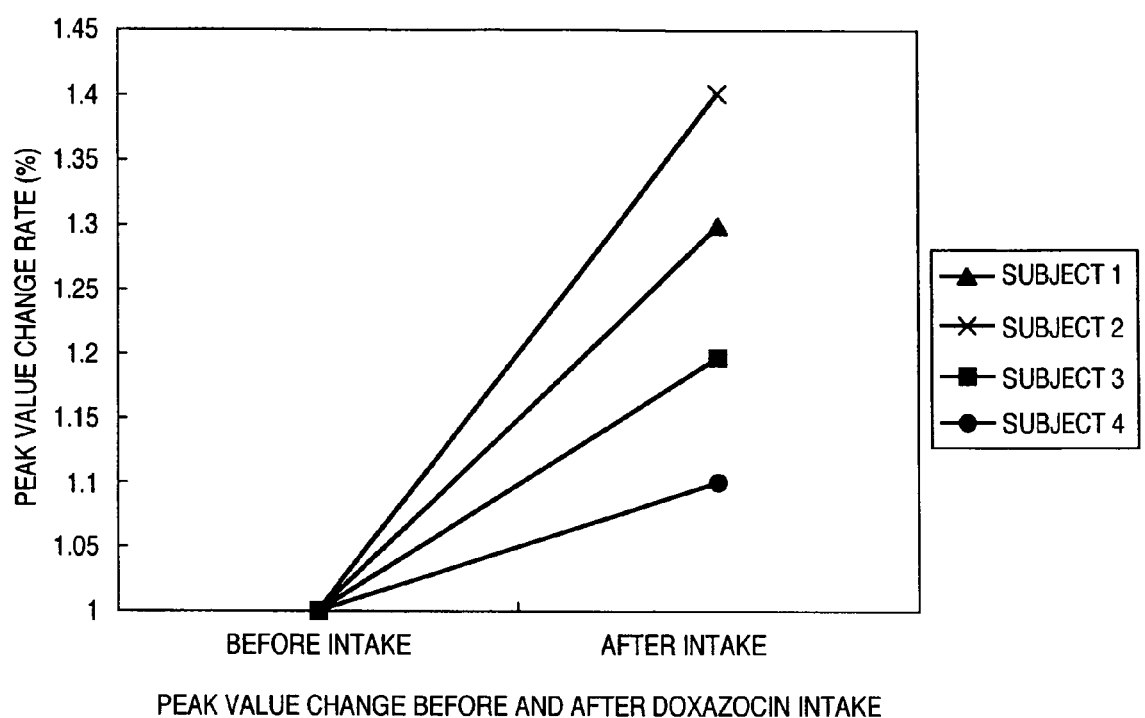
FIG. 7 is a diagram showing changes of peak values of signal waveforms before and after intake of doxazocin.

There are reports that the cerebral blood flow is increased and the cerebral auto regulation is improved by that action. As to a change corresponding to the movement of such a cerebral blood flow improving medicine as well, it becomes possible to monitor it on the basis of the time curves of the peak value and latency of the hemoglobin signal waveform measured a plurality of times as shown in FIG. 7 without using the SPECT (single photon emission CT). In FIG. 7, a result obtained by monitoring an increase of the cerebral blood flow in a plurality of testees four weeks after intake of doxazocin is shown collectively.

Figure 8A:
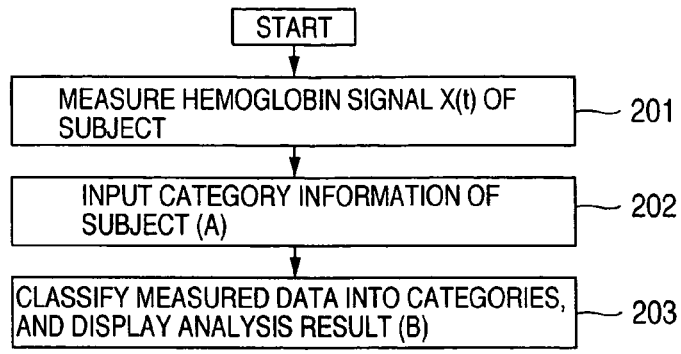
FIGS. 8A to 8C are flow diagrams showing an embodiment of data analysis using a living body light measuring device according to the present invention.
Figure 8B:
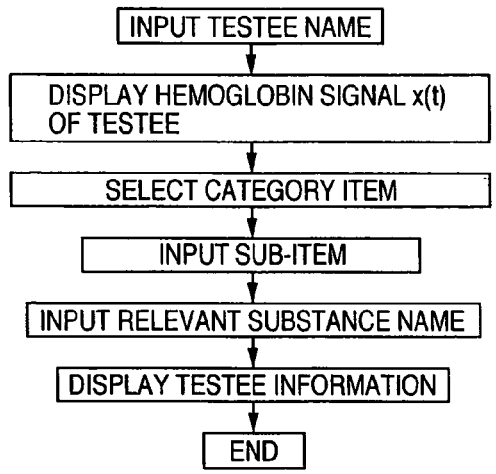
Figure 8C:
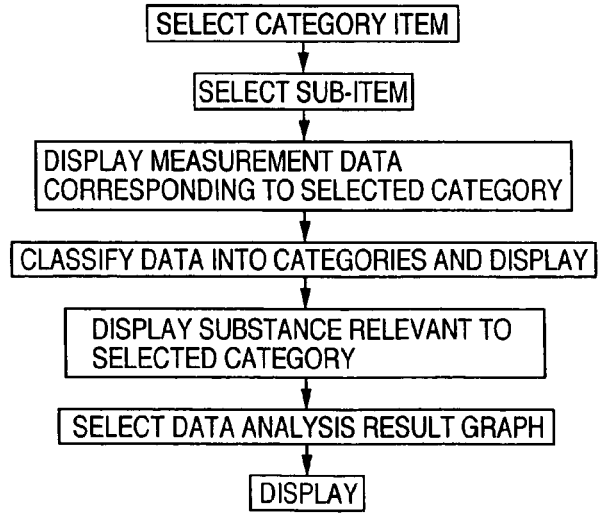

An embodiment in the case where a large number of data measured under various inspection conditions are analyzed in the living body light measuring device will now be described. FIGS. 8A to 8C are flow diagrams showing its procedure.

The above-described embodiment has been described taking the case where the inspection item is the ALDH2 genotype as an example. However, possible inspection items in the living body light measurement are diversified. Furthermore, inspection conditions such as the subject information are also diversified. They include categories, for example, physical characteristic traits, such as the height, weight and blood type, the intake substance, genotype, disease, character, and stress level. In the living body light measuring device according to the present invention, therefore, the hemoglobin signal is measured for each of testees (step 201), and then measured data are classified into categories by the category processor 23, and recorded in the storage 22 (step 202). The category processor 23 accepts category input of object measurement data, selects measurement data of a specified category, and analyzes the measurement data (i.e., delivers the data to the hemoglobin signal processor 21) (step 203).

The step 201 shown in FIG. 8A is similar to the step 101 in the embodiment shown in FIG. 2. In the step 201 as well, the case where the inspection item is the ALDH2 genotype is taken as an example. The category input step 202 is implemented using an input screen exemplified in FIG. 9. This input screen includes an input section 3-1 for inputting subject information, a Display button 3-2, a measurement data display section 3-3, a category item selection section 3-4, a sub-item input section 3-7, a relevant substance input section 3-10, a testee information display section 3-13, and a Finish button 3-14. If subject information (such as a name and an ID) concerning a specific subject for which measurement has been finished is input and the Display button 3-2 is operated, measurement data of the subject are displayed in the measurement data display section 3-3.

In the category item selection section 3-4, a plurality of category items previously registered in the storage 22 are exhibited. One or more categories can be selected from among them. It is possible to additionally register a new item and delete in item that has become unnecessary by operating an Add button 3-5 and a Delete button 3-6 on the input screen.

The sub-item is input when it is necessary to classify some category into further subordinate categories. Furthermore, the relevant substance is input when the category is relevant to an intake substance as in the ALDH2 genotype. As for the sub-item and relevant substance as well, sub-items and relevant substances previously stored in the storage 22 may be exhibited and selection may be conducted from among them. As for the sub-item and relevant substance as well, the user can conduct addition and deletion by operating the Add button and the Delete button, respectively.

If an inspection category and, as occasion demands, a sub-item and a relevant substance are input as to a specific subject, then the input information is displayed in the testee information display section 3-13. If the user ascertains contents and operates the Finish button 3-14, then input testee information is stored in the storage 22 together with measurement data.

Figure 10:
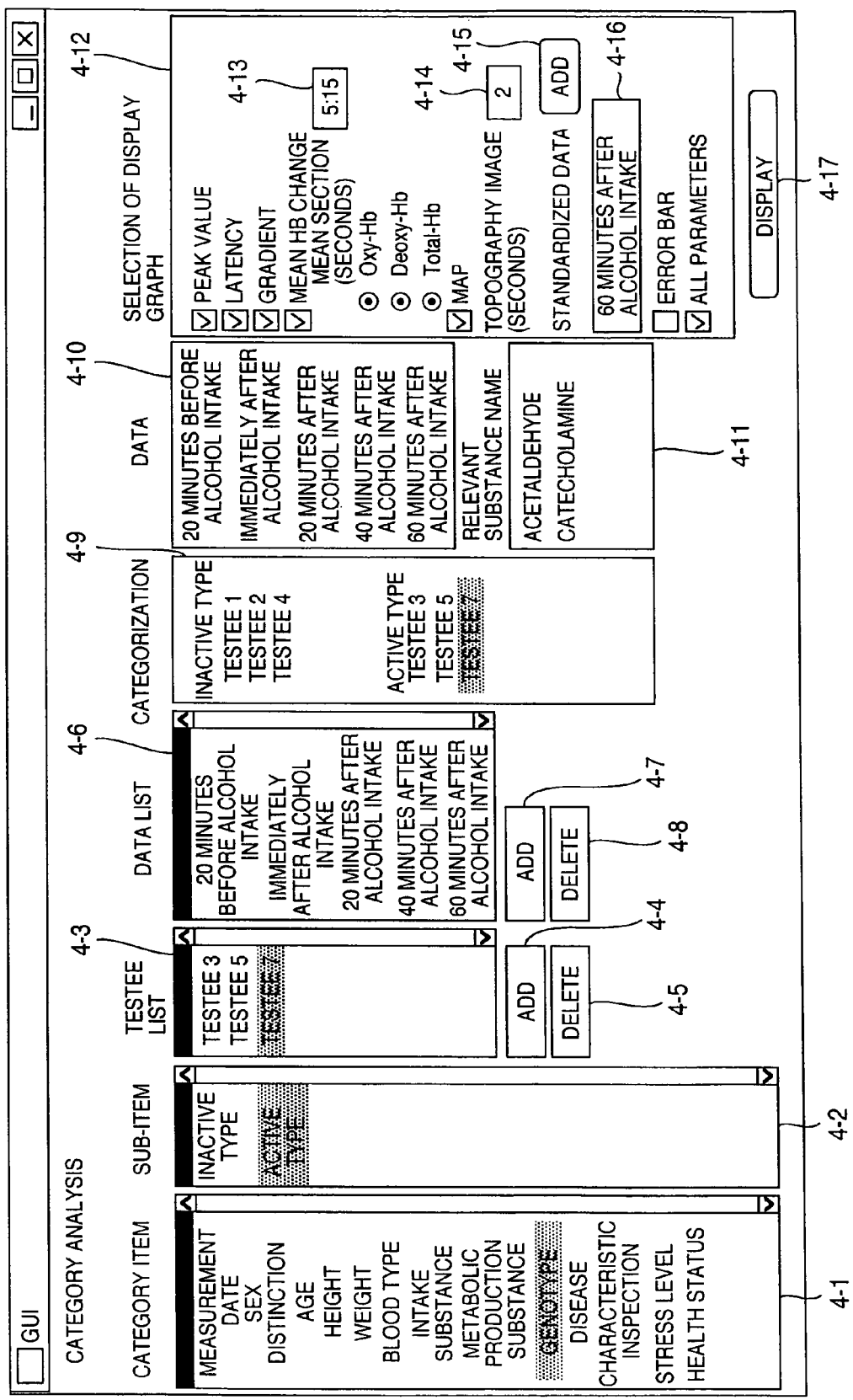
FIG. 10 is a diagram showing a category information input screen in the embodiment shown in FIGS. 8A to 8C.

The measurement data thus stored in the storage 22 include data measured under various inspection conditions. In the living body light measuring device according to the present embodiment, therefore, the user specifies data to be displayed and the display is conducted (step 203). FIG. 10 is a diagram showing an input screen for specifying display information.

The illustrated input screen serves also as a screen for inputting a category analysis command. The input screen includes a category item selection section 4-1, a sub-item selection section 4-2, a testee selection section 4-3, a data selection section 4-6, a category display section 4-9, a data display section 4-10, a relevant substance display section 4-11, a display graph selection section 4-12, and a Display button 4-13.

When conducting category analysis via this input screen, the user first selects one arbitrary item from among inspection categories displayed in the category item selection section 4-1. The categories displayed in the category item selection section 4-1 are categories input as testee information and stored in the storage 22 in the living body light measuring device until then. If a category is selected, then sub-items are displayed in the sub-item selection section 4-2 according to the selected category, and a sub-item can be selected. If an inspection category or a sub-item is selected, a list of testees having measurement data recorded under the selected item is displayed in a testee selection section 4-3. Therefore, the user selects an arbitrary testee to be analyzed.

If a testee is selected, measurement data of the testee are displayed in the data selection section 4-6 as a list. Data required for the analysis is selected from the list.

As for lists displayed in the testee selection section 4-3 and the data selection section 4-6, addition and deletion can be conducted suitably by operating Add buttons 4-4 and 4-7 and Delete buttons 4-5 and 4-8, respectively.

If data to be selected is specified from among data stored in the storage 22 by operation heretofore described, then the selected category, the measurement data, and the relevant substance name are displayed in the category display section 4-9, the data display section 4-10 and the relevant substance display section 4-11, respectively.

A list of graphs and images that can be displayed is displayed in the display graph selection section 4-12 together with check boxes. In addition, an input section 4-16 for adding and inputting data that is not included in the list, and input sections 4-13 and 4-14 for specifying display conditions (range, time resolution, and space resolution) with respect to some graphs and images are provided. The user selects check boxes in the list displayed in the display graph selection section 4-12, and sets necessary conditions.

The signal processor 21 accepts this setting operation as a command, and analyzes measurement data (signal waveform) included in the specified category (step 203). For example, if the inspection item is the ALDH2 genotype and the peak value and latency are selected as the parameters, the parameters are found from signal waveforms thus classified, at the step 102, and graphs of time curves are generated. Results of the analysis conducted in the signal processor 21 are displayed on the result viewer 25.

Figure 11:
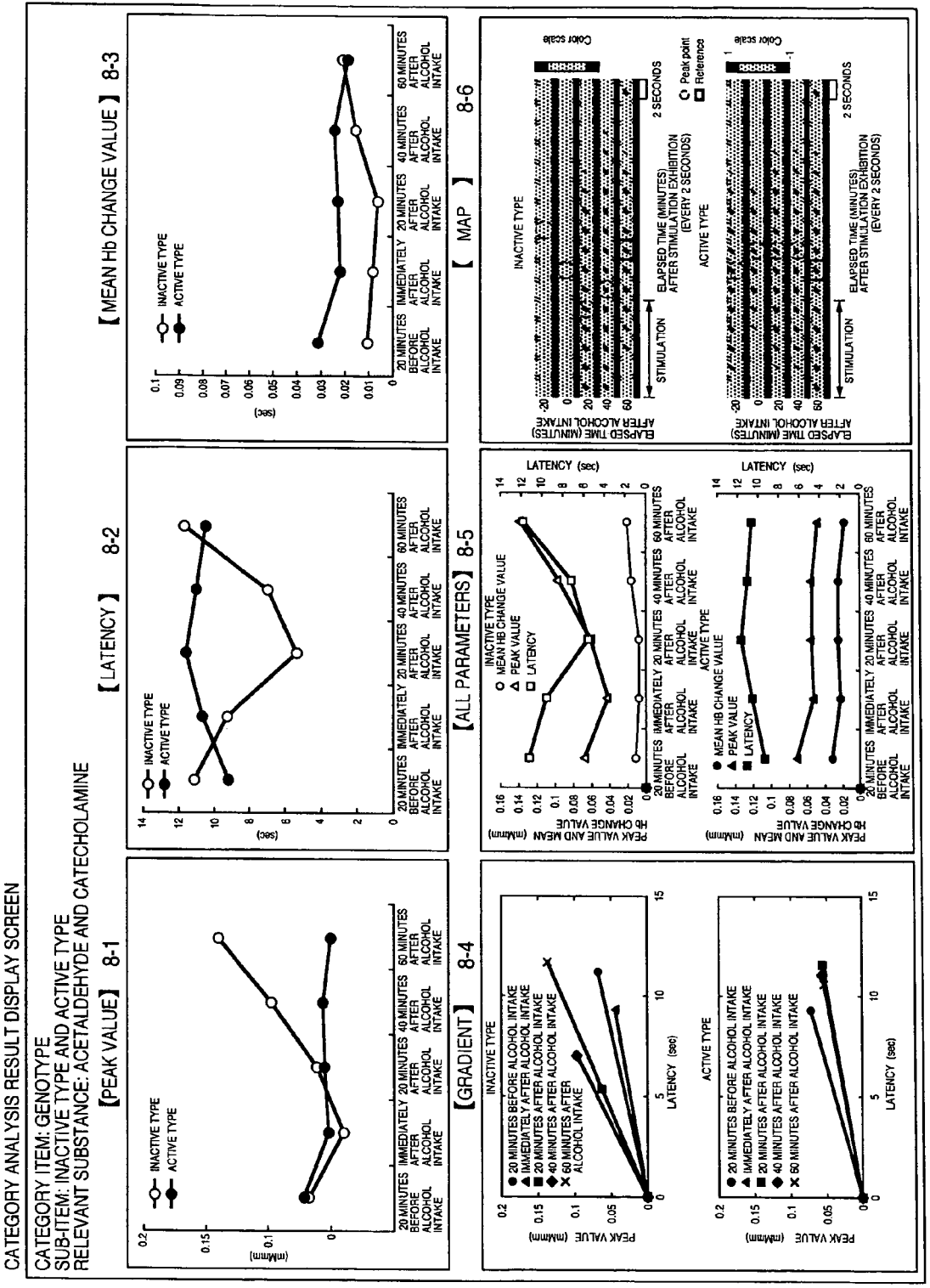
FIG. 11 is a diagram showing an analysis result display screen in the embodiment shown in FIGS. 8A to 8C.

FIG. 11 shows an example of a resultant image displayed in the display section 25. In the illustrated example, the genotype is selected as the category item, and the inactive type and the active type are selected as the sub-items. With respect to measurement data of corresponding testees, a time curve 8-1 of the peak value, a time curve 8-2 of the latency, and a time curve 8-3 of a mean value of hemoglobin change quantity within a definite time period are displayed on the upper side of the display section. Gradients 8-4 having the peak value as the ordinate and the latency as the abscissa, graphs 8-5 obtained by dividing all parameters into the inactive type and the active type, and maps 8-6 are displayed on the lower side. In the maps 8-6, the ordinate represents measurement points in time in the case where measurement is conducted a plurality of times, whereas the abscissa represents a hemoglobin change quantity standardized using the peak value obtained 60 minutes after alcohol intake as reference, in a topography image every two seconds. In 8-4 to 8-6, the upper column shows the inactive type and the lower column shows the active type.

Thus, according to the present embodiment, results of a plurality of parameters can be compared at a time by categorizing and analyzing measurement data measured under diversified inspection conditions. Furthermore, since only the selected category can be analyzed, the analysis processing time can be shortened. In addition, it is possible to assist in understanding the relevancy between the blood component concentration and inspection items and parameters optimum to judging characteristic traits of the testee, i.e., the physiological meaning of the parameters by using the analysis function in the present embodiment.

According to the present invention, the living body light measuring device is provided with the function of displaying time curves of parameters found from the signal waveform, and consequently a time curve of a metabolic substance or an intake substance can be monitored. Furthermore, it also becomes possible to judge characteristic traits of the subject on the basis of the time curve graph. In addition, according to the present invention, the living body light measuring device is provided with the function of classifying data measured under diversified inspection conditions into categories, storing the classified data, and analyzing a selected category, and consequently the analysis time can be shortened. Furthermore, the living body light measuring device according to the present invention can be useful for comparing a large number of parameters at a time and understanding physiological meaning of the parameters.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A living body light measuring device comprising:

light measuring means for applying light to a subject and receiving light reflected or transmitted by a head of the subject;

signal processing means for drawing a change of a blood substance when a trial is given to the subject a plurality of times, as a signal waveform on the basis of a measurement signal received by said light measuring means;

result viewer means for displaying a result of processing conducted by said signal processing means; and input means for sending a command to said signal processing means, wherein said input means comprises means for inputting specification of a specific inspection item among a plurality of inspection items which are contained in a blood flow of the subject and change as time elapses, said signal processing means extracts at least one feature corresponding to a specific inspection item specified by said input means, and causes said result viewer means to display a time curve of the feature as a graph, and said signal processing means comprises:

storage means for storing data, the data accumulating relations between sub-items belonging to the inspection item and the time curve; and screening means for judging characteristic traits of the subject on the basis of the graph and a change rate of the accumulated data in the graph obtained as to the subject.

2. A living body light measuring device according to claim 1, wherein a viewer of said result viewer means is a graph having time as an abscissa axis thereof and a value (feature quantity) obtained by converting the feature to a numerical value as an ordinate axis thereof.

3. A living body light measuring device according to claim 1, wherein the inspection items are classified according to an intake substance of the subject, and data measured at predetermined time intervals comprise data before and after substance intake time of the subject.

4. A living body light measuring device according to claim 1, wherein the characteristic trait is an ALDH2 genotype of the subject, the specific inspection item is a blood aldehyde concentration, the change rate is a change rate of peak values or latency time periods of the blood aldehyde concentration, and the subject is judged as an active type, if the change rate of peak values or latency time periods is below a predetermined value.

5. A living body light measuring device according to claim 1, wherein the characteristic trait is an intake of medicine, the specific inspection item is a blood flow change, the change rate is a change rate of peak values or latency time periods of a blood aldehyde concentration, and the subject is judged as intaking the medicine in a desired manner, if the change rate of peak values or latency time periods is above or below a predetermined value.

6. A living body light measuring device according to claim 5, wherein the medicine is a vasodepressor.

7. A living body light measuring device according to claim 6, wherein the vasodepressor is trapidil.

8. A living body light measuring device according to claim 5, wherein the medicine is doxazocin.

* * * * *